US006221094B1

United States Patent
Bare

(10) Patent No.: US 6,221,094 B1
(45) Date of Patent: Apr. 24, 2001

(54) RESONANT FREQUENCY THERAPY DEVICE

(76) Inventor: James E. Bare, 8005 Marble Ave., NE., Albuquerque, NM (US) 87110

( * ) Notice: Subject to any disclaimer, the term of this patent is extended or adjusted under 35 U.S.C. 154(b) by 0 days.

(21) Appl. No.: 09/175,458

(22) Filed: Oct. 20, 1998

Related U.S. Application Data

(63) Continuation-in-part of application No. 08/784,794, filed on Jan. 16, 1997, now Pat. No. 5,908,441.

(51) Int. Cl.[7] .................................................. A61N 1/02
(52) U.S. Cl. .................................. 607/1; 607/2; 607/88; 607/156
(58) Field of Search .................................. 607/1, 2, 145, 607/150, 151, 154–156, 88–93, 100, 101, 115; 606/27, 29

(56) References Cited

U.S. PATENT DOCUMENTS

| | | |
|---|---|---|
| 4,112,923 * | 9/1978 | Tomecek .................. 600/11 |
| 4,119,102 | 10/1978 | LeVeen . |
| 4,315,514 | 2/1982 | Drewes et al. . |
| 4,336,809 * | 6/1982 | Clark ........................ 606/13 |
| 4,366,809 | 1/1983 | Trexler . |
| 4,545,368 | 10/1985 | Rand et al. . |
| 4,680,749 | 7/1987 | Englund et al. . |
| 4,852,086 | 7/1989 | Eastmond et al. . |
| 4,955,083 | 9/1990 | Phillips et al. . |
| 5,224,942 * | 7/1993 | Beuchat et al. .............. 606/15 |
| 5,300,068 | 4/1994 | Rosar et al. . |
| 5,402,782 | 4/1995 | Lodder . |
| 5,553,610 | 9/1996 | Lodder . |
| 5,591,219 * | 1/1997 | Dungan ....................... 607/88 |
| 5,676,695 | 10/1997 | Di Mino et al. . |
| 5,830,211 * | 11/1998 | Santana et al. ............. 606/27 |

* cited by examiner

Primary Examiner—Linda C. M. Dvorak
Assistant Examiner—David M. Ruddy
(74) Attorney, Agent, or Firm—Hoffman Wasson & Gitler PC

(57) ABSTRACT

A generator of a complex energy wave, having audio, radio and light components, including an audio frequency oscillator, a radio frequency transmitter, a radio frequency amplifier, an antenna tuner, an antenna, tuned coaxial cables and an optional reverberation unit.

14 Claims, 3 Drawing Sheets

RESONANT FREQUENCY THERAPY DEVICE

This application is a continuation-in-part of Ser. No. 08/784,794, filed Jan. 17, 1997, now U.S. Pat. No. 5,908,441.

BACKGROUND OF THE INVENTION

1. Field of the Invention

This invention relates to surgical devices. More specifically, the present invention relates to radiative type surgical devices.

2. Description of the Prior Art

Organisms are able to absorb or store energy which later may be converted into useful work, heat or re-radiated. In the event energy is absorbed faster than the subject may utilize it, or re-radiate it, excess energy builds up. When an organism is under the influence of an energy wave having frequency equal to the resonant frequency of the organism, the organism, or at least some resonant part of it, continues absorbing energy. At the point where too much energy is absorbed, the energy begins to cause failure in the structure absorbing the energy. At resonance, this process of structural failure occurs very quickly. This may easily be seen by exposing Paramecium Caudatum to the present device when operating at 1150 Hertz (Hz). The normally very motile organism literally stops motion while changes occur in the protoplasm until a point in the cell wall fails.

The energy associated with this process is described by the formula, $E=hv$, which is applicable to ultraviolet light, X-rays, and radiation on various molecules. "E" symbolizes energy content, "h" represents Planck's constant and "v" stands for the frequency in cycles per second.

Electromagnetic waves include visible light, heat, X-rays, radio waves and the like. These are all merely different frequencies of the electromagnetic spectrum, and as such have different properties. Each may be amplified, diminished, changed in frequency, radiated or even heterodyned. Heterodyning is the combining of two dissimilar waves to produce two new waves. One of the new waves is the sum of the two frequencies, the other new wave being the difference of the frequencies.

The use of audio, radio and light waves to treat diseased tissue is well known in the arts. Audio wave-type devices typically employ a piezoelectric ultrasonic generator driven by a radio frequency amplifier coupled to an ultrasonic lens of known focal length. The locus of cells to be destroyed is ascertained through known pulse-echo imaging techniques. Once the locus of target cells is fixed, the lens is focused on the target area and the intensity of the ultrasound is increased to a level sufficient to affect tissue destruction by thermal heating. An example of this technique is shown in U.S. Pat. No. 4,315,514, issued Feb. 16, 1992, to William Drews et al.

Radio wave-type cell destroying devices typically employ amplitude-modulating transmitters in series with an amplifier, tuner and antenna for training high power radio waves on a target area. As with the above device, the intensity of the radio waves increases to a level sufficient to affect tissue destruction by thermal heating.

Light wave-type cell destructive devices typically employ lasers, constructed by known means, which also are trained only a target locus of cells. The high intensity light waves deliver light energy of an intensity sufficient to affect destruction of the cells by a thermal heating.

The use of various electrical wave forms in therapeutic applications is well know. Square Waves, Triangle waves, Sine waves and other similar wave shapes are used in electrical stimulators to treat physical ailments and stimulate physiologic processes. The problem inherent to all these forms of electrical waves is that the wave tends to travel over lines of least resistance in the body, often bypassing the intended area of treatment. Conductive gels, selective placement of electrodes, high voltage-low current, alternating polarity, and the use of beat frequencies with interferential electrical waves, are among some of the methods used in order to overcome this limitation of electrical treatment.

There are other devices that attempt to gain better tissue acceptance of the therapeutic wave forms. Modulated Shortwave diathermy, modulated ultrasound, and infrasound units all have made attempts at getting better tissue acceptance of the therapeutic wave. Yet all these types of application again suffer from either poor tissue acceptance, poor penetration, or tissue resistance-accommodation effects of the therapeutic wave.

Each of the above devices have been somewhat effective in destroying living cells, but, individually, are not fully compatible with the complex nature of living cell tissue. As a testament to this, some analytical tools have been developed which simultaneously apply different kinds of wave energy. For example, in U.S. Pat. No. 5,402,782, issued Apr. 4, 1995, and U.S. Pat. No. 5,553,610, issued Sep. 10, 1996, both to Robert A. Lodder, similar devices are disclosed which simultaneously apply to a subject, a magnetic field, near-infrared radiation and an acoustic wave. Collection of the electrical, acoustical and near-infrared spectra provides much more comprehensive data that is more useful in the treatment of the subject.

Although multi-component wave generating devices have been used for analytical purposes, none are used for affecting cell destruction. Owing to the complex nature of biological cells, a need exists for a resonant frequency therapy device providing for the transmission of multiple wave energies.

None of the above references, taken alone or in combination, are seen as teaching or suggesting the presently claimed resonant frequency therapy device.

SUMMARY OF THE INVENTION

The present invention overcomes the limitations of the above inventions by providing a resonant frequency therapy device which delivers a complex transmission of energy waves comprising audio, radio and light waves, possibly generating a fourth type of wave. The invention includes known components, namely an audio frequency oscillator, a radio frequency transmitter, a radio frequency amplifier, an antenna tuner, an antenna, tuned coaxial cables and an optional reverberation unit.

This is a new method of application of therapeutic electrical waves. This method relies upon shaping an overmodulated radio wave pulse in a radio transmitter and then outputting that pulse into a gas filled tube. The gas within the tube is then excited by the overmodulated radio energy, and the wave form output from the gas filled tube will penetrate and couple to all tissues in the patient producing physiologic effects based upon the applied audio frequency.

In consideration of the above, a first object of the invention is to provide a resonant frequency therapy device for destroying cell malignancies.

A second object of the invention is to provide a resonant frequency therapy device which may be constructed from inexpensive readily available materials.

A third object of the invention is to provide a resonant frequency therapy device which combines diverse wave energies and generates a composite energy wave which may be used to treat malignant cells.

A fourth object of the invention is to provide a resonant frequency therapy device which may break down microorganisms.

A fifth object of the invention is to provide a means of stimulating the circulating white blood cells into a state of hypermobility.

A sixth object of the invention is to provide a device that repels or drives insects from an area.

A seventh object of the invention is to provide improved elements and arrangements thereof in an apparatus, for the purposes described, which is inexpensive, dependable, and effective in accomplishing its intended purposes.

These and other objects of the present invention will become readily apparent upon further review of the following specification and drawings.

BRIEF DESCRIPTION OF THE DRAWINGS

Similar reference characters denote corresponding features of the invention consistently throughout the attached drawings.

DETAILED DESCRIPTION OF THE PREFERRED EMBODIMENTS

The present device incorporates a phenomenon known as harmonics in its operation to trigger the resonant characteristics of target cells or organisms. A harmonic is a multiple of the original (fundamental) frequencies of wave functions. For example, a second harmonic of 100 cycles is 200 cycles or Hz while a third harmonic would be 300 cycles.

The invention employs square shaped wave functions which are made up of an infinite number of the odd numbered harmonics fundamental frequency. That is, a square wave is constructed from sine waves using the third, fifth, seventh and so on, harmonics of the fundamental frequencies. For example, a 1000 cycle fundamental output square wave contains sine waves of 3000 Hz, 5000 Hz, 7000 Hz, and all other odd numbered harmonics.

The invention employs an amplitude modulated (AM) radio wave which comprises three waves, the primary wave and two side bands which are the sum and difference of the radio wave and the modulated audio wave. For example, a 1000 cycle audio wave on a 1,000,000 cycle radio wave produces two side bands; one, the lower side band at 999,000 cycles, and two, the upper side band at 1,001,000 cycles. The separation between the upper and lower side bands is what is known as the bandwidth. In this example, the bandwidth is 2000 cycles. The harmonics that make up the audio frequency square wave will produce the bandwidth of the transmitted electromagnetic wave, which will play an important part in the construction and operation of the present invention.

The side bands are important in that they contain all of the square waves generated. The side bands contain only one third of the power of the total electromagnetic energy generated and transmitted, while the carrier wave retains the other two thirds of the power transmitted. All of the harmonics that make up the square wave also will produce side bands of their own. Further, a linear amplifier will produce harmonics of the primary input radio wave generated by the transmitter used in the present invention. These harmonics of the radio wave also will act as a carrier of all the harmonics of the square wave and produce another set of side bands, thus resulting in literally hundreds of radio and audio frequencies produced by and introduced into a plasma tube antenna, discussed below. The effects of the device are dependent upon the properly applied audio frequency. It is the audio frequency that determines the formation of side bands, and the ability to produce resonant interaction between the device and the selected tissues or microorganisms. Therefore with the proper audio frequency resonant effects occur, and with the incorrect audio frequency, there are no effects.

Figure 1:
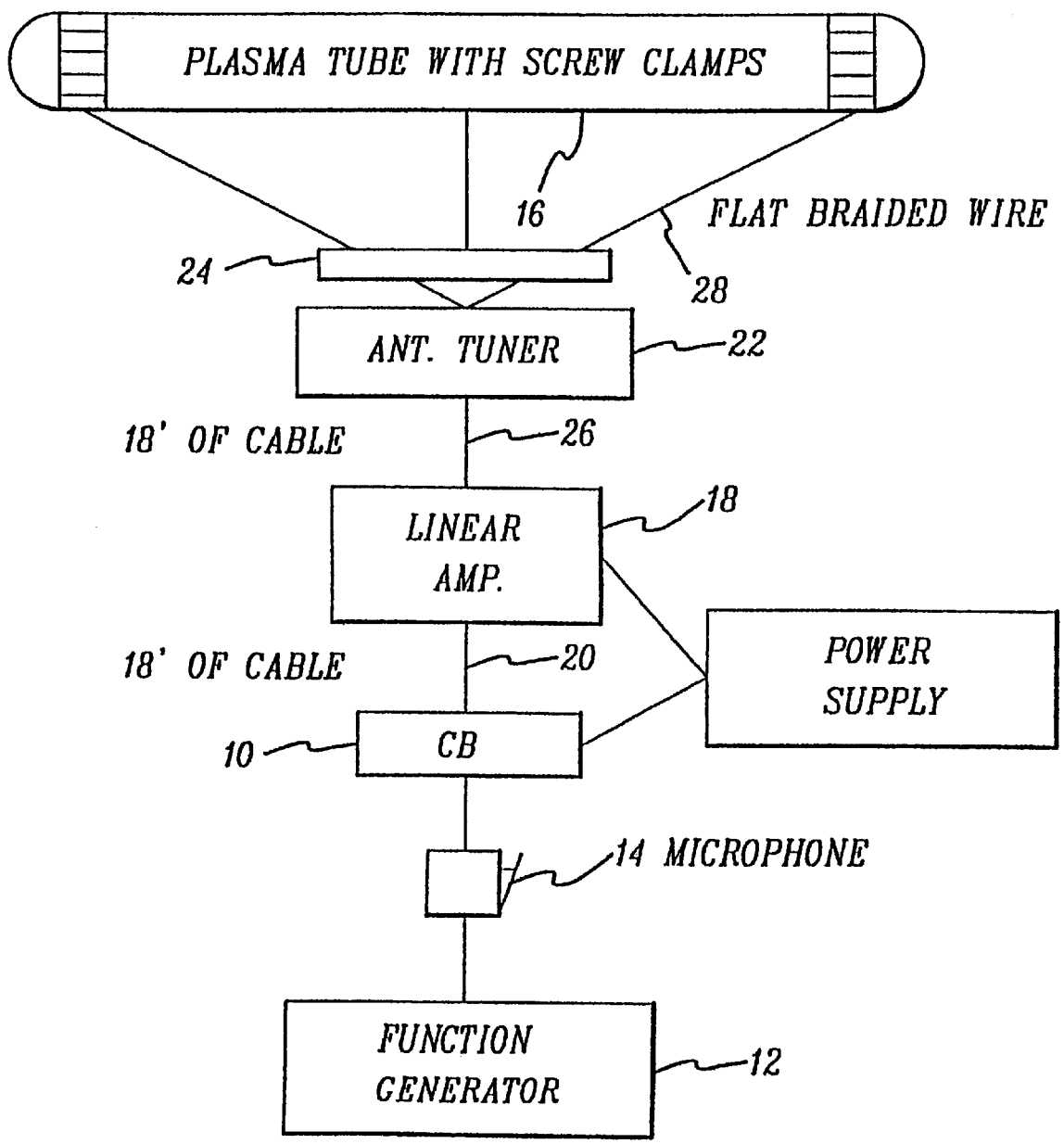
FIG. 1 is a diagrammatic view of the invention.

Referring to FIG. 1, the device includes a low power radio frequency transmitter 10 generating radio waves having a radio frequency and a radio function. The radio frequency utilized generally is in the 2 to 33 MHZ range. It has been found that certain radio frequencies may produce deeper tissue penetration with the device than other radio frequencies. The radio frequency used to excite the plasma may of course be varied as necessary to achieve optimal effects. The FCC has set aside certain frequencies for use with industrial, scientific and medical (ISM) devices. The most commonly used of these is located at 27.12 MHZ. The allocated bandwidth by the FCC at 27.12 MHZ is + or −163,000 cycles or a total of 326,000 cycles. It is to the devices advantage to utilize all this available allocated bandwidth in its operation.

The primary low power radio frequency transmitter must be Amplitude Modulated preferably on a frequency of 27.12 MHZ. The simplest method to generate the necessary 27.12 AM radio wave is to utilize a standard Citizen Band (CB) radio set to operate on channel 14. CB radios generally include audio filters that limit the audio frequency response to a range of 300 to 2500 cycles. This frequency limitation effectively inhibits and clips off the harmonics in the square wave. To overcome this frequency limitation, modifications are made to the CB radio that widens its bandwidth. Further, the modulation limiter of the CB radio is bypassed allowing the CB radio to over-modulate. Over-modulation produces a pulsed radio wave.

This pulse will of course have a positive and negative aspect. But once in the patients body the wave will demodulate, normally passing only the positive half of the wave into the tissues. By carefully shaping the overmodulated radio energy pulse, the radio energy pulse can be made to resemble the input wave form. When the wave demodulates within the tissues, the wave will once again be present in it's applied shape.

The limitation of this method is that the modulated frequency and the power of the radio energy must be of sufficient intensity to fully penetrate and permeate the tissues. Too little radio energy power, will cause a lack of penetration. Too little audio energy on the carrier wave will cause a lack of permeation or saturation of the tissues with the therapeutic audio wave. It has been found as a rule of thumb, that providing the audio is fully modulated, about one watt of RF power per pound of body weight is necessary for full penetration and optimum effects. The advantage of this method is that one can bypass any of the resistance effects of electricity, and that all the harmonics forming the original shaped audio wave are allowed to pass into the body cells without inhibition or distortion.

When the radio wave is modulated with an audio signal, the audio wave will therefore be pulsed too. The effects of pulsed radio frequency energy on tissues is well known. The unique effect generated by the modified CB radio is that the pulse width and duration varies directly with the modulated audio frequency square wave. The higher the audio frequency modulated, the shorter and more frequent the output pulse of radio energy.

The duration of each pulse is dependent of the duty cycle of the input wave form, and the duty cycle of the radio wave pulse. Generally the two duty cycles should correspond closely. The radio pulse should always be longer in time than the modulated wave pulse. For example if a 1000 Hz audio square wave of 50% duty cycle is introduced to the radio, the total time between each square wave would be 1 millisecond, and the time the square wave would be on is but 0.5 ms. The radio pulse should correspond closely to the audio timing and in this example, this would be anywhere from about 0.52 ms to 0.62 ms in length. There is an optimum timing for the radio pulse length based upon the duty cycle of the applied modulated wave. Either too long or too short a radio pulse will diminish the physiologic effects of the therapeutic wave.

Experimentation with different duty cycles of the applied audio wave indicate that an audio duty cycle of 50% or less will tend to produce optimal effects at most audio frequencies. The use of greater than a 50% audio duty cycle is of course possible, but optimal effects are currently derived at 50% audio duty cycle or below.

The RF duty cycle may exceed 90% at extremely low applied audio frequencies, that is below 200 Hz. As one approaches 20 Hz the radio duty cycle may approach or exceed 95%. This long RF duty cycle seems to optimize the output wave, but only at extremely low audio frequencies. Above 300 Hz, the audio and the Rf duty cycles generally are very closely matched in duration.

The audio wave may also be gated, it has been found that this generally is at a rate of from about 0.5 to 4 times a second. Presently, a close to optimal audio gate rate, seems to be about 0.75 seconds on and then 0.75 seconds off. Or one complete on-off cycle every 1.5 seconds. The gating of the audio wave creates a gate effect of the radio wave pulses, the number of radio pulses generated per gating sequence is dependent upon the applied audio frequency. If the audio frequency was 1,000 Hz then each full radio pulse would be 1 ms. With a 0.75 second on gate, 750 radio pulses would pass before the gate closed. Gating of a radio pulse is not new, but using the gate to control a shaped RF wave output to a plasma tube is a new application.

The invention also employs an audio frequency oscillator 12 generating audio waves having an audio frequency and an audio function. The audio frequency oscillator 12 must provide for square wave output and should be adjustable in multiple range steps for frequency. Preferably, the quality of the square wave is quite high, being less than 0.1% distorted.

The square wave should have a rise time of less than 20 nanoseconds, the faster the rise time the better. The audio frequency oscillator may be connected to the AM transmitter directly or to the microphone 14 of the transmitter.

One way to deliver optimum voltage output to the microphone is to listen to the output of the CB unit on another CB and set the output voltage to produce a clear signal. A second way is to set the output of the square wave generator to below 0.2 volt, then set the plasma tube antenna 16 to near maximum brightness by increasing or decreasing the voltage out of the frequency generator. Once set for one frequency, the voltage output should be correct for all audio frequencies. A third way is to employ a wide band oscilloscope to set the voltage output to the microphone at its optimum level.

Ideally, the radio frequency transmitter delivers a pulsed wide band width radio wave with a pulse rate and width varying with the applied audio frequency. Also, the radio frequency amplifier should deliver power in an amount that increases as the audio frequency increases.

Stability in audio frequency output may not be necessary toward optimum usage of the invention. Recent investigation has shown that frequency instability may be more effective. Toward this end, the invention may include means for presetting the degree of drift or sweep across a certain set amount of audio frequencies.

One may also sweep the audio frequency from a starting to an ending point, or may waver the audio frequency back and forth across a set value. The rate at which the frequency changes within the swept or wavered sequence, has been shown to enhance effects. Generally this is about 0.5 to 6 seconds per Hz. If the frequency changes too fast, there is not sufficient time for the wave to create changes and effects are not optimal. If the frequency changes too slowly, the physiologic effect of the sweep is lost. The patients body will respond in a manner similar to using a set continuous frequency and then changing to a new frequency. The use of a sweep and waver has been used in other prior devices but not with a shaped wave output through a radio frequency excited gas plasma.

Where a high powered AM radio transmitter is used, the invention includes the use of a wide band width linear radio frequency amplifier. A wide bandwidth linear amplifier is necessary in order to properly amplify the side bands generated by the primary radio frequency generator. Preferably the linear radio frequency amplifier has no harmonic suppression and will generate its own radio frequency band harmonic signals. The linear amplifier receives and amplifies the output radio wave from the primary transmitter. From the amount of amplification produced by the linear amplifier, a power multiplication factor can be determined. This power multiplication factor in a 200 watt output linear amplifier being driven by a 4 watt output CB radio is equal to 50. The power multiplication factor is important in giving power to the side bands generated by the input audio square wave. For example, a harmonically generated side band of the fundamental square wave audio frequency may have only one-half watt of power as it leaves the CB radio. After passing through the linear amplifier this same side band now has 25 watts of power.

Between the radio frequency transmitter and the radio frequency amplifier, the invention employs a discrete length of coaxial wire 20. The length chosen is crucial in that the invention is most effective where transmission occurs with a minimum of standing wave ratio. Standing wave ratio is a measure of the power absorbed by the antenna relative to the power reflected back to the radio frequency amplifier. The ideal ratio is 1:1, however anything below 2:1 is good. A standing wave ratio that is too high will destroy the amplifier as well as the transmitter. Ideally, the cable length should be 18 feet or ½ wavelength long. The use of an 18 foot or ½ wavelength cable between the primary radio transmitter and the linear amplifier has been found to facilitate the creation of a gas plasma within the plasma tube.

The invention also includes an antenna tuner 22. The antenna tuner matches the output of the radio frequency amplifier to the plasma tube 16 to insure that the maximum power is transmitted to the tube. The tuner receives the output from the radio frequency amplifier and supplies it via the wire terminals of the antenna tuner to the antenna leads of the plasma tube.

In order for the antenna tuner to function, it must be set on the lowest inductance regardless of the type of tube or gas used. Once the plasma lights in the plasma antenna, the standing wave ratio will approach infinity briefly until the plasma begins absorbing the power. At that point, the tuner knobs may be used to bring the standing wave ratio to a minimum. If the plasma does not light, input to the transmitter should be ceased temporarily to prevent damage to the primary radio frequency transmitter and linear amplifier.

Optionally, the invention may employ an external balun 24, an impedance matching transformer used in some antenna tuners. The balun plays an important role in the full generation of the plasma waves of interest. A balun is rated by its ability to match dissimilar circuits. For example, a 4:1 balun will match a 75 ohm to a 300 ohm circuit. The size and type of balun has a direct effect on the strength and field density of the wave produced by the device. It has been found that certain baluns containing a large toroid can produce local fields that are physically difficult to tolerate for more than a few minutes at a time.

The invention employs a second length of coaxial cable 26 interposed between the radio frequency amplifier and antenna tuner. Ideally, the cable should be 18 feet or ½ wavelength long. The use of said 18 foot or ½ wavelength long cable tends to orient the output wave from the plasma tube fore and aft rather than laterally relative to the plasma tube.

No direct contact of the plasma tube is necessary with the device. One merely has to be within the active field emanated from the tube in order to achieve effects. Currently this active field extends at least 60 feet from the tube making exposure and treatment of large groups of people or animals very easy. This technique of application to large groups of people has been placed in current usage and has proven it's efficacy with over 50 people at one time.

The antenna tuner delivers energy to the antenna via approximately four feet of antenna wire 28. The standing wave ratio should be maintained under 2:1 to prevent damage to the electronics.

The invention employs a plasma tube 16 as an antenna. The antenna 16 generates an output signal. A plasma tube antenna allows exposure of the entire subject, or a room full of subjects at one time.

No direct contact of the patent with the plasma tube is necesary with the device. One merely has to be within the active field eminated from the tube in order to achieve effects. Currently this active field extends at least 60 feet from the tube making exposure and treatment of large groups of people or animals very easy. This technique of application to large groups of people has been placed in current useage and has proven it's efficacy with over 50 people at one time.

Any of three types of glass may be used: First, common leaded glass found in any neon tube shop; second, quartz; and third, borosilicate (pyrex). Leaded glass is the easiest to work, is of the lowest cost and fastest to fabricate. Leaded glass is not ideally suited for the present invention because it is not very strong and tends to obstruct ultraviolet light.

Quartz glass is very strong, passes the entire light spectrum and has high heat resistance. Unfortunately, quartz is very expensive and generally does not accept internal electrodes. Bombardment, or purification of a finished quartz tube by heating it with flame or electrical current while evacuating it, is quite difficult without internal electrodes. Pyrex, on the other hand, does accept metal inserts of kovar or tungsten.

Enhanced effects of this invention have been noted in using different tube lengths, internal gas pressures of the tubes, tube volumes per unit length, how the is coupled to the tube, and the gasses that the tubes are filled with. To a point the larger the volume of the gas in the tube, the higher the pressure of the gas in the tube, and the longer the tube, the better have been the observed effects. If the gas pressure is too high, the volume is too large, or the tube is too long, effects can be severely diminished.

One must also match the applied radio power to the size of tube. Heat is generated by the application of radio energy to the tube, and too small a diameter, too small a volume or length of tube will decrease effects of this method. One also risks melting and perforation of the glass envelope. The inventor on one notable development day, managed to destroy three tubes within a hour from too much power and heat.

The tube may be filled with any noble gas (Argon, Helium, Neon, Xenon or Krypton). Argon, Helium and Neon give off ultraviolet radiations when excited by high voltage electricity. In order to fully utilize the spectrum of these gases, unleaded glass must be used. Diluting the primary gas with another gas reduces the amount of voltage necessary to create lighting of the plasma, commonly known as Penning affect. Experimentation with a mixture of about 98% Helium and 2% Argon has shown to be a very easily lightable mixture.

The type of gas within the plasma tube has been shown to show different physiologic effects with the device. Some gasses such as neon will produce primarily light waves in the near infrared region, other gasses or mixtures will produce light waves in the ultra violet region such as argon gas or an argon/mercury vapor mixture.

It has been found that a mauve color of the plasma seems to produce overall the highest physiologic effects. One can create this color with mixtures of argon and neon gasses, or with pure argon gas. The color is partially derived from the gas pressure in the tube, the applied audio frequency and radio energy power, the volume of the tube, and the way the RF energy is introduced into the tube.

As the tube forms a plasma, a compressed "bar" of plasma will form within the interior of the tube. Argon gas needs to have a very thin and narrow "bar" to produce the mauve color. Argon/neon gas does not need such tight compression of the bar to produce the mauve color.

Table 1, below, contains a number of spectral lines and their position in the infrared, visible and ultraviolet regions for the noble gases.

TABLE I

Number of Spectral Lines

| GAS | TOTAL | VISIBLE | >7050 (IR) | <3950 (UV) |
|---|---|---|---|---|
| Argon | 383 | 164 | 110 | 109 |
| Helium | 129 | 26 | 47 | 57 |
| Krypton | 260 | 77 | 130 | 53 |
| Neon | 439 | 82 | 153 | 204 |
| Xenon | 309 | 130 | 132 | 47 |
| Mercury[1] | 195 | 41 | 32 | 122 |

[1]Mercury is not a noble gas.

Visible light generally exists between 3950 and 7050 angstroms. Accordingly, Neon provides comparatively little visible strength yet it is the brightest of the noble gases in the visible region when excited by radio frequencies.

Below, Table 2 shows the range of spectral lines for each of the gases.

TABLE II

Range of Spectral Lines

| GAS | RANGE |
|---|---|
| Argon | 487 to 23,966 |
| Helium | 231 to 40,478 |
| Krypton | 729 to 40,685 |
| Neon | 352 to 33,834 |
| Xenon | 740 to 39,955 |
| Mercury[1] | 893 to 36,303 |

[1]Mercury, when added to the above gases, may decrease the power necessary to initiate the lighting of the plasma.

It is well known that a shorter wavelength, in Angstroms, will provide for a more powerful spectral wave. Between 100 and 1000 angstroms, the wave has enough power to produce photoionization of $O_2$, O, $N_2$, and N. Between 1000 and 3000 angstroms, the spectral wave has enough power to photodissociate $O_2$ and $O_3$. Generally, germicidal ultraviolet radiation occurs between 2200 and 2950 angstroms. The most effective transmission commonly used being 2537 angstroms.

Table III, below, lists the typical amount of germicidal energy necessary to destroy common microorganisms. Significantly, all of the gases of interest produce spectral lines far below the 2537 angstrom level. These spectral lines can be of use only if utilizing either quartz or more silicate glass for the plasma tube.

TABLE III

Germicidal Energy

| BACTERIAL ORGANISM | UV ENERGY (uw-sec/cm$^2$) |
|---|---|
| B. Anthracis (Anthrax) | 4520 |
| Salmonella Enteritidis (Food Poisoning) | 4000 |
| C. Diphtheriae (Diphtheria) | 3370 |
| E. Coli (Food Poisoning) | 3000 |
| N. Catarrhalis (Sinus Infection) | 4400 |
| P. Aeruginosa (Various Infections) | 5500 |
| Dysentery Bacilli | 2200 |
| Staph. Aureus (Various Infections) | 2600 |
| Strep. Viridans (Various Infections) | 2000 |

It is currently hypothesized that some of the reason for the physiologic effects noticed with gating of the audio wave may be due to a reverse EMF that the body creates. That is if one considers the tissues to have an inductance, then when the wave turns off, a reverse EMF is generated which has effects different from just using a continuous output of pulsed RF.

Recent testing with a Hall effects sensor seems to indicate the presence of bodily magnetic fields at certain applied audio frequencies within the devices field. It is hypothesized that this method of introducing shaped wave forms may be producing Nuclear Magnetic Resonance effects in the bodies tissues. Meaning that a new method of the generation of NMR may possibly be derived from the use of this method of application of waveforms.

In the use of MRI instruments which measure and correlate NMR in the body to produce internal pictures, the radio wave is varied in frequency, the magnetic field may be varied in intensity, and the pulse width is generally kept static. Most MRI units use an RF pulse width of around 20 ms.

In this invention, the RF pulse width varies with the applied audio frequency, but keeps the radio frequency fixed. However there is no reason that one could not vary the radio frequency keeping the audio frequency fixed, and thus the pulse width fixed, or one could also vary the audio frequency with the radio frequency. Which ever method or combination there of would be necessary to optimize effects. The LARMOR frequency of NMR is determined by the following equation:

$$y\ Ho\ v = - - - 2\ pi$$

Where
   v=frequency in cycles per second
   Ho=strength of the magnetic field
   y=the gyromagnetic ratio–26,750
If one considers the relatively weak magnetic field of the earth (about 0.5 gauss) or of the devices EMF as static, then using the above equation, it can be seen that NMR effects will occur at audio frequencies. For example in the earths magnetic field of 0.5 gauss, NMR effects should occur at 2129.7 Hz.

Utilizing the linear amplifier of the present invention, the plasma tube may produce approximately 125,000,000 microwatts of power entering the plasma tube, the actual power being modulated by the light waves being unknown. The result in transmitted power, measured especially in the UV region, at this time, is not directly ascertainable. The light energy given off may be measured with various well known instruments, but the measurement does not truly indicate the power of the UV wave.

Table IV below, shows the total sum strength of the spectral electromagnetic light waves emitted by each type of gas in the UV, visible and infrared bands. The table also shows the number of spectral lines having a strength of 1000 or more. Spectral line strength is relative and compared to the standardized weakest observable line, which is 1.

TABLE IV

Electromagnetic Light Wave Strength

| GAS + # LINES > 1000 | EM BAND STRENGTH | TOTAL FOR GAS |
|---|---|---|
| Helium | UV 4843 | 11,901 |
| # Lines = 5 | Visible 1416 | |
|  | IR 5742 | |
| Krypton | UV 12,370 | 151,290 |
| # Lines = 45 | Visible 38,910 | |
|  | IR 100,010 | |
| Mercury | UV 38,761 | 55,371 |
| # Lines = 9 | Visible 9950 | |
|  | IR 6660 | |
| Xenon | UV 12,370 | 168,326 |
| # Lines = 46 | Visible 55,040 | |
|  | IR 93,329 | |
| Neon | UV 30,526 | 266,823 |
| # Lines = 86 | Visible 6712 | |
|  | IR 212,795 | |
| Argon | UV 17,015 | 418,460 |
| # Lines = 32 | Visible 33,549 | |
|  | IR 382,837 | |

Other gases, that have not been examined due to toxicity and/or chemical reactivity, include Fluorine, Bromine and Chlorine. Each gas has certain aspects which are very appealing for use. For example, Bromine has nearly 10 times the UV output of Mercury, 9 times the visible output over Xenon and about 2.5 times the IR output of Argon. Due to the chemical reactivity of these gases, they should never be used in a tube with an internal electrode, probably only in a quartz tube with ultraviolet shielding.

The internal electrodes of the plasma tube may vary quite a bit. If using standard or common Neon sign tubing, cold cathode type electrodes with flexible woven connecting leads for power input should be used. Electrodes with solid copper connecting leads will quickly break the wire lead. The two internal electrodes are known as a cathode and an anode. The anode in this unit should be a piece of round barstock with a sloping face on it, attached to the tube. The cathode may be a piece of the same round barstock except that it generally has a flat face perpendicular to the anode support. The anode has an angle on its face between 17° and 22°. The greater the anode angle, the more energy required for a particle to leave the face of the anode parallel to the cathode face. The narrower the anode face angle, the less energy that is needed for a particle to leave the anode face parallel to the cathode face. As a result, the main beam comes out of the tube at a glancing angle, instead of at 90°, therefore the subject being treated will have to be positioned accordingly.

Figure 5:
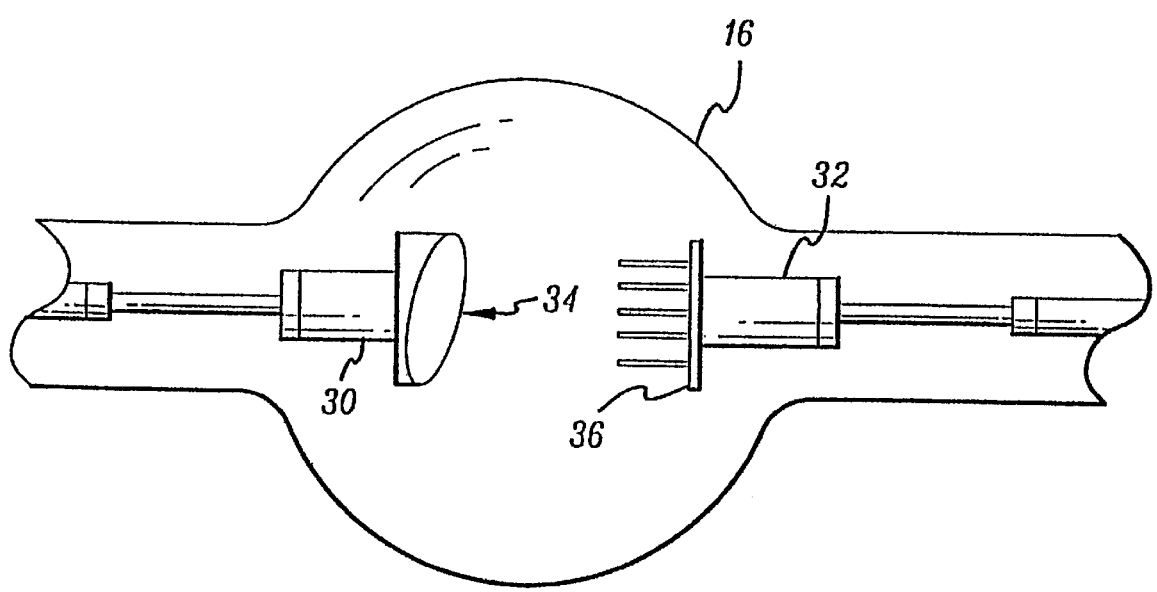
FIG. 5 is a diagrammatic view of an alternative embodiment of an antenna used with the invention.

The cathode may be formed with a point in the center of it to better disperse the radio frequency energy. The cathode may be nothing more than a pointed tip at the end of the support rod. The cathode also may be round and flat faced with multiple sharp needles projecting outward toward to anode. As a rule, the anode and cathode should not be placed nearer than 1 cm. apart, preferably around 2.5 cm. apart. This is exemplified in FIG. 5. The tube 16 is shown containing anode 30 and cathode 32. The anode 30 has a flat angled face 34. The cathode 32 has a flat face 36 with a plurality of sharp needles 38 projecting therefrom.

The anode and cathode should be constructed from non-porous, heat-tolerant material, such as steel, stainless steel, tungsten, kovar, tantalum or nickel/chrome-plated brass. Porous metals, such as silver, gold, brass, tin, aluminum and copper, trap small amounts of gases and impurities that may leak into the tube over time and contaminate it. Further, the electrodes do become quite hot under the influence of radio frequency, thus some metals may melt, destroying the tube.

Figure 2:
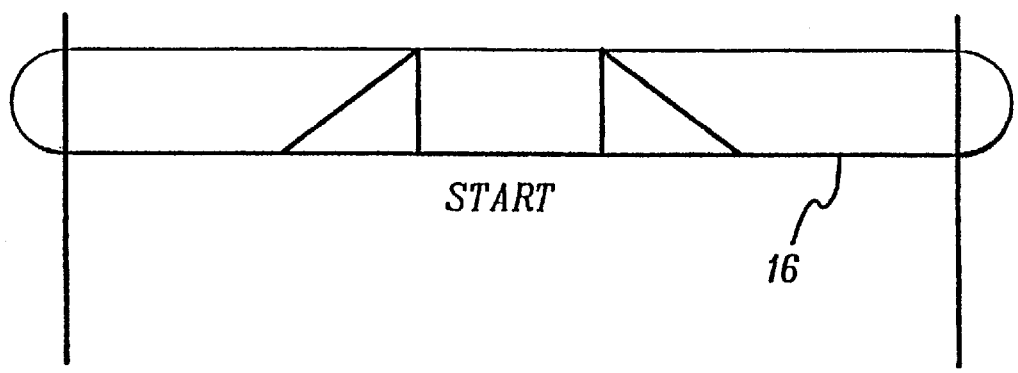
FIG. 2 is a diagrammatic view of an embodiment of an antenna used with the invention.
Figure 3:
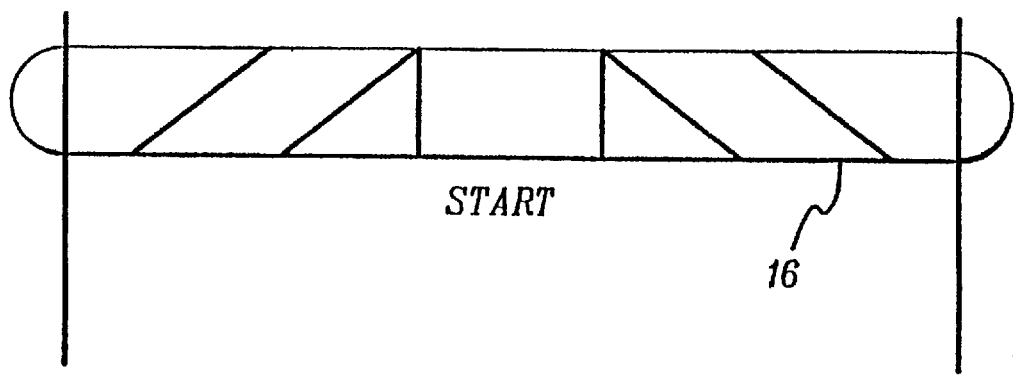
FIG. 3 is a diagrammatic view of an embodiment of an antenna used with the invention.
Figure 4:
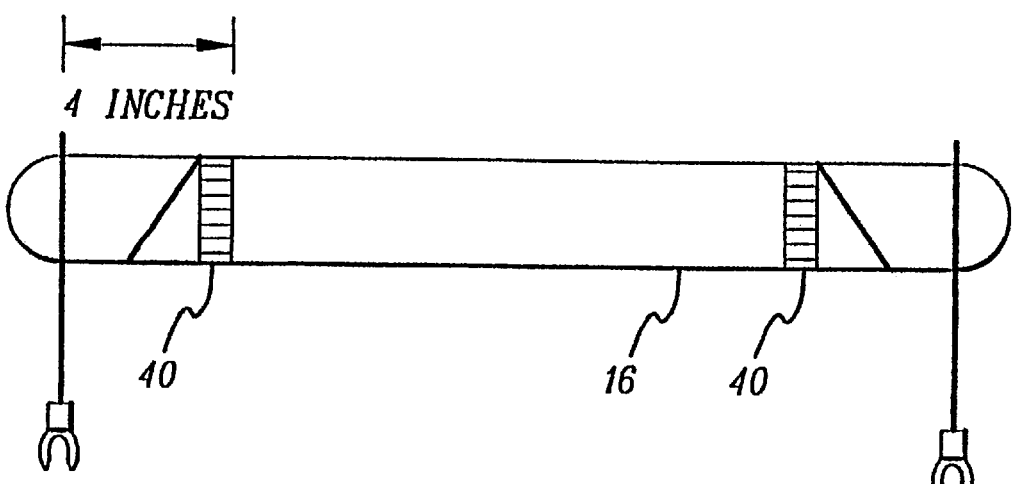
FIG. 4 is a diagrammatic view of an alternative embodiment of an antenna used with the invention.

If a tube without electrodes is used to practice the invention, the tube must be wrapped with a flat braided wire. This is best seen in FIGS. 2, 3 and 4. Referring to FIG. 4, the tube should be wrapped with approximately one turn of wire before two automotive hose clamps 40 are mounted on the tube, securing the wire thereto. Preferably, on a 16-inch long tube, the clamps should be located approximately 12 inches apart. Another method would be to attached the wire to the electrodes at the end of the tube. This method is not recommended because of the difficulty in lighting the gas.

Referring to FIG. 2, wrapping the tube with a spiral of wire is possible, but care must be taken in doing so. This method may produce a condition in which the plasma tends to twist and distort and in some cases, not light. If not done properly, too much current density prevents plasma. Argon-filled tubes seem to work well with this method.

A focused metallic reflector behind the tube tends to help direct the light waves and intensify some of the devices effects.

The precise nature of a plasma wave, the energy produced in a plasma tube, is not clear. One theory has it that the radio wave, with its attached or modulated audio wave, is attached to the light generated in the plasma tube. Possibly, the light waves are modulated onto the radio-audio waves. Yet another theory is that an entirely new form of energy is created which has properties common to sound, light and radio waves, but also properties which are not common.

Within the plasma tube, the audio frequency is spread about longitudinally, the light travels in longitudinal waves and the radio waves are disbursed vertically or horizontally from a standard antenna. The vector interface of these three forms of vibration in cellular structures may be a contributing factor in the device's ability to cause the devitalization of small organisms. The heterodyning occurring within the plasma tube also may account for literally thousands of different frequencies.

The magnetic field component in an RF wave travels transversely, and the electrical wave component travels vertically. It is unknown how the wave emanating from the plasma tube travels. It is hypothesized that the wave from the plasma tube may be of a magnetic nature.

Although the above has been directed primarily toward eradication of malignant cells, the device also may be employed for other beneficial purposes. During development of the present device, it was observed that insects were irritated by the transmitted waves. Although sustained large doses transmitted waves may be lethal to human beings, experimentation with frequency and power levels should result in a device that is harmless to humans, yet annoying to insects such that they are driven from an area, such as a house or farmer's field. The output signal of the present device may be directed toward an insect population to drive them from a location.

The present invention is not intended to be limited to the embodiments described above, but to encompass any and all embodiments within the scope of the following claims.

I claim:

1. A therapeutic method for treating a tissue comprising the steps of: exposing the tissue to an output signal of a gas plasma the gas plasma formed by subjecting a gas to:

an audio wave having an audio frequency; and a radio wave having a radio frequency.

2. A method as recited in claim 1, the output signal further comprising a light wave having a light frequency, the frequency of the light varying with the type of gas, the audio frequency and radio frequency.

3. A method as recited in claim 1, wherein said audio wave is a square wave.

4. A method as recited in claim 1, wherein said radio wave is pulsed to excite the gas into a plasma.

5. A method as recited in claim 4, wherein said radio wave is pulsed at the frequency of the audio wave to excite the gas into a plasma.

6. A method as recited in claim 4, wherein a duration of each radio wave pulse varies with a frequency of said audio waves.

7. A method as recited in claim 4, wherein a power of the output signal is proportional to the audio frequency.

8. The method of claim 1, wherein one watt of radio frequency power is used per pound of body weight of a patient.

9. The method of claim 1, wherein the audio wave is gated.

10. The method of claim 9, wherein the gate is at a rate of 0.5 to 4 times a second.

11. The method of claim 1, wherein the plasma has a mauve color caused by exciting argon gas.

12. The method of claim 3, wherein said square wave has a variable duty cycle.

13. A method for treating tissue, comprising:

providing a gas in a tube, exciting the gas into a plasma to create a signal, and exposing tissue to the signal created by the gas plasma, wherein the gas is excited into a plasma by applying an audio wave and a radio wave to the tube.

14. The method of claim 13, wherein the gas plasma signal is pulsed by pulsing said radio wave and audio wave.

* * * * *